United States Patent
Pugh et al.

[19]

[11] Patent Number: 5,861,306
[45] Date of Patent: Jan. 19, 1999

[54] MULTI-WELL BONE CULTURE DEVICE FOR USE IN ASSESSMENT OF BONE CELL ACTIVITY

[75] Inventors: Sydney M. Pugh, Glenburnie; Timothy J. N. Smith, Kingston, both of Canada

[73] Assignee: Millenium Biologix, Inc., Canada

[21] Appl. No.: 847,889

[22] Filed: Apr. 28, 1997

Related U.S. Application Data

[63] Continuation of Ser. No. 518,912, Aug. 24, 1995, abandoned.

[51] Int. Cl.$^6$ ............................................. C12M 3/00
[52] U.S. Cl. ............................. 435/288.4; 435/299.2; 435/305.1; 435/305.2; 435/326; 435/372; 435/402
[58] Field of Search .................. 435/287.1, 288.3, 435/288.4, 299.2, 305.1, 305.2, 305.3, 305.4, 326, 372, 402

[56] References Cited

U.S. PATENT DOCUMENTS 3,726,764  4/1973  White .
3,745,091  7/1973  McCormick .

FOREIGN PATENT DOCUMENTS 9426872   11/1994  WIPO .............................. C12M 3/04
WO9426872 11/1994  WIPO .

OTHER PUBLICATIONS

"Failure of Cells of the Mononuclear Phagocyte Series to Resorb Bone", Chambers, et al., Calcified Tissue International, 1984, pp. 556–558.

"The resorption of biological and non–biological substrates by cultured avian and mammalian osteoclasts", Jones, et al., Anatomy and Embryology, 1984, pp. 247–256.

"Resorption of Dentine by Isolated Osteoclasts in vitro", Boyde, et al., Br. Dent J. 1984, pp. 216–220.

"The effect of substrate composition and condition on resorption by isolated osteoclasts", Shimizu, et al., Bone and Mineral, 6 (1989), pp. 261–275.

"An Assay System Utilizing Devitalized Bone for Assessment of Differentiation of Osteoclast Progenitors", Amano, et al., Journal Of Bone And Mineral Research, vol. 7 No. 3, Mar. 1992, pp. 321–327.

"Resorption Of Bone By Isolated Rabbit Osteoclasts", Chambers, et al., J. Cell. Sci. 66, 1984, pp. 383–399.

Primary Examiner—David A. Redding
Attorney, Agent, or Firm—Bell Seltzer Intellectual Property Law Group of Alston & Bird LLP

[57] ABSTRACT

The present invention describes a multi-well bone cell culture device for use in the quantitative and/or qualitative assessment of bone cell activity, the device comprising a flat base having a sintered film of calcium phosphate entities on one side and an open-ended multi chamber unit positioned on top of the film which by a sealing means is sealed to the film coated base forming individual containment wells. The device is useful in the analysis of bone cell function, for the screening and determination of bone cell disease, and the development of drugs to alter bone cell activity.

8 Claims, 5 Drawing Sheets

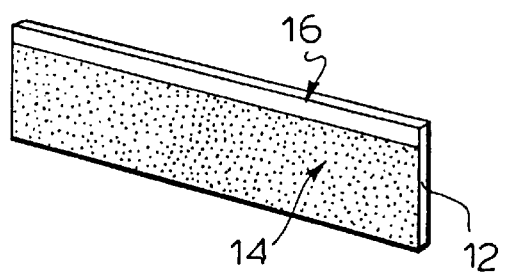
FIG. 2B.
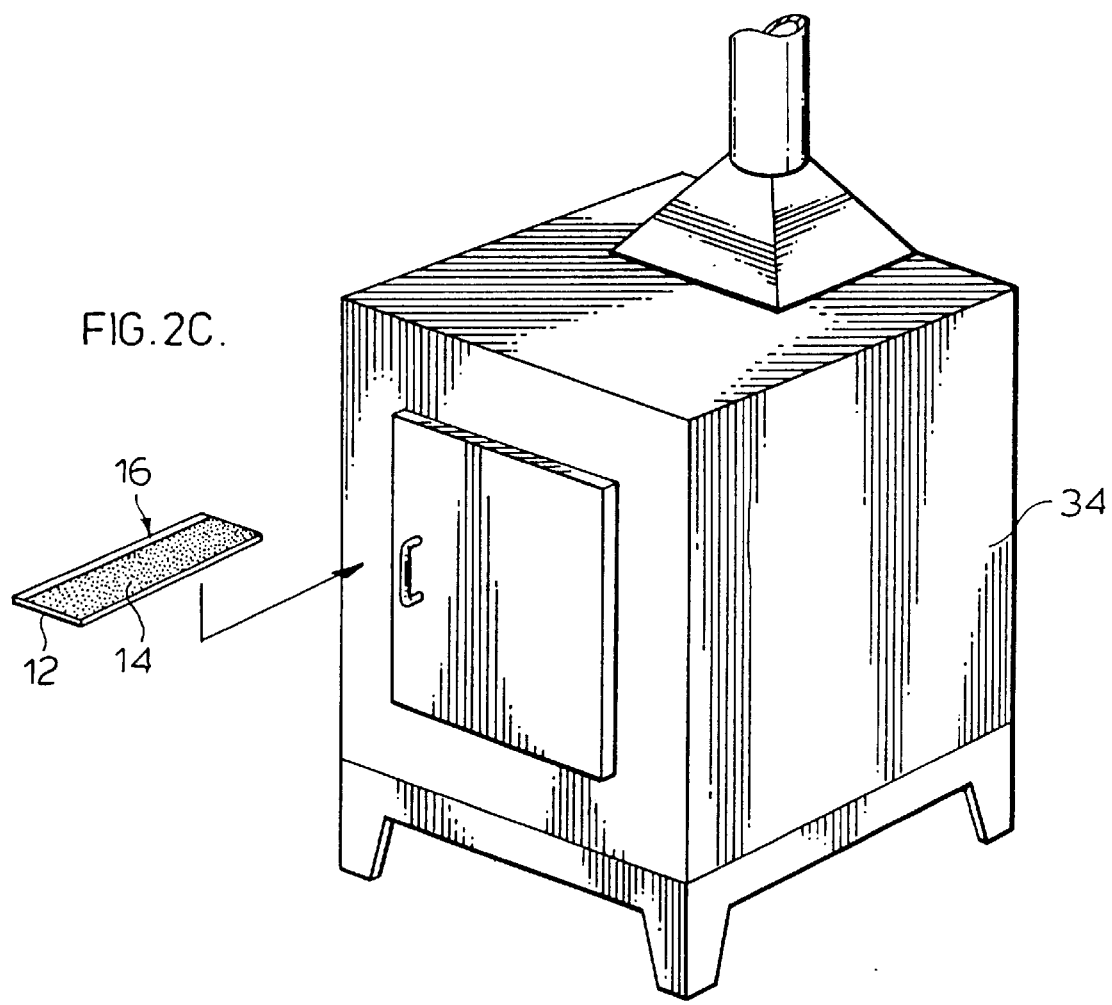
FIG. 2C.
FIG. 3.
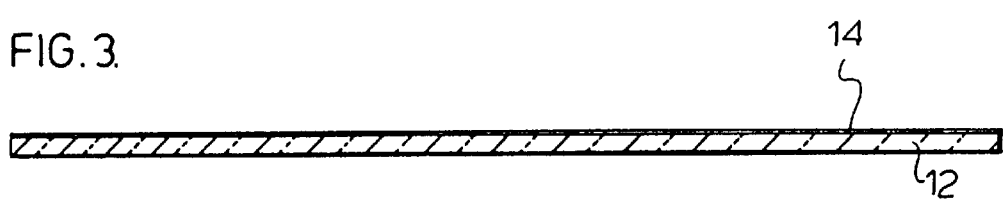

FIG.8.
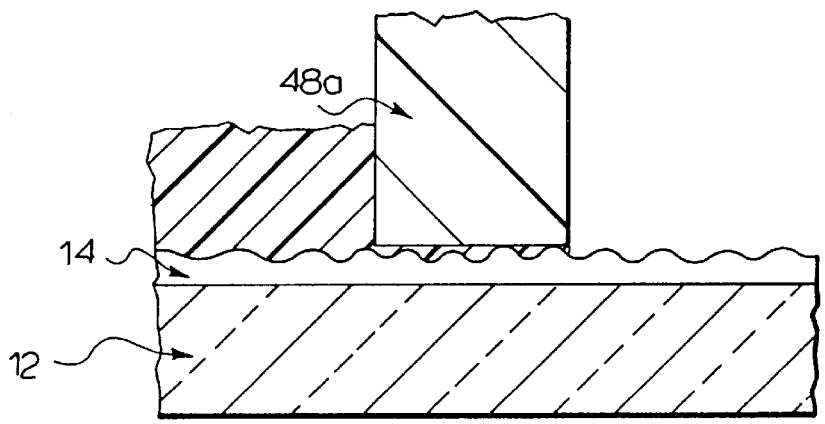
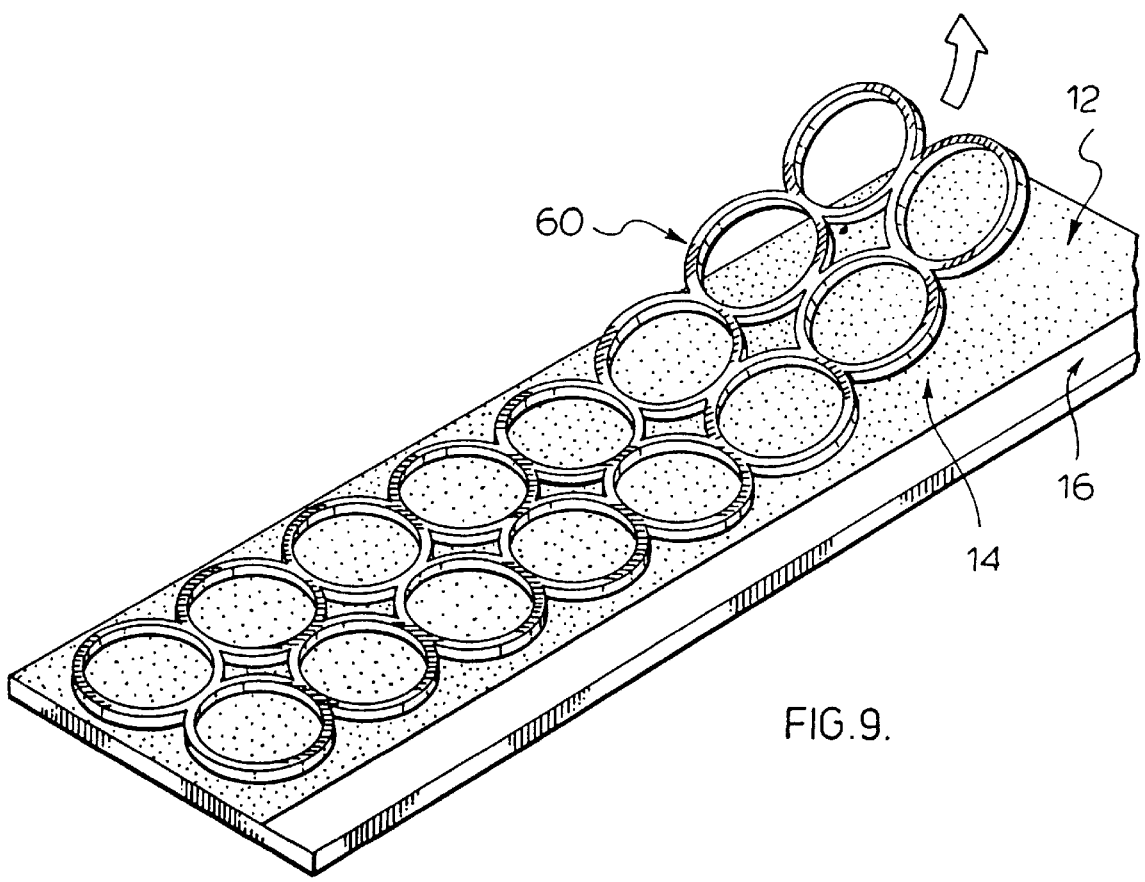
FIG.9.

MULTI-WELL BONE CULTURE DEVICE FOR USE IN ASSESSMENT OF BONE CELL ACTIVITY

This application is a continuation of application Ser. No. 08/518,912, filed 24 Aug., 1995 now abandoned.

FIELD OF THE INVENTION

This invention relates to the development of a multi-well bone cell culture device for use in the assessment of bone cell activity, such as osteoclast and osteoblast activity which is useful in the analysis of bone cell function in health and disease. Such bone cell activity assessment assists in the determination of bone diseases, such as osteoporosis or osteitis fibrosa in humans, and also in the idenification of novel drags effective in altering bone cell activity which would allow for the development of therapies for the treatment of bone diseases.

BACKGROUND OF THE INVETION

Bone is a complex mineralizing system composed of an inorganic or mineral phase, an organic matrix phase, and water. The inorganic mineral phase is composed of crystalline calcium phosphate salts while the organic matrix phase consists mostly of collagen and other noncollagenous proteins. Calcification of bone depends on the close association between the organic and inorganic phases to produce a mineralized tissue.

The process of bone growth is regulated to meet both structural and mechanical stresses. The cells involved in the processes of bone formation, maintenance, and resorption are osteoblasts, osteocytes, and osteoclasts. Osteoblasts synthesize the organic matrix, osteoid, of bone which after calcium phosphate crystal growth and collagen assembly becomes mineralized. Osteocytes regulate the flux of calcium and phosphate between the bone mineral and the extracellular fluid. Osteoclasts functions to resorb bone and are essential in the continuous process of bone remodelling. Disturbing the natural balance of bone formation and resorption leads to various bone disorders. Increased osteoclast activity has been demonstrated to lead to bone disease characterized by a decrease in bone density such as that seen in osteoporosis, osteitis fibrosa and in Paget's disease. All of these diseases are a result of increased bone resorption.

In order to understand the mechanisms involved which regulate bone cell functioning, it is important to be able to assess the normal function of bone cells and also the degree of perturbation of this activity in various bone diseases. This will lead to the identification of drugs targeted to restore abnormal bone cell activity back to within normal levels.

Several research groups have developed methods to directly observe the activity of isolated osteoclasts in vitro. Osteoclasts, isolated from bone marrow cell populations, have been cultured on thin slices of natural materials such as sperm whale dentine (Boyde et al Brit. Dent. J. 156, 216, 1984) or bone (Chambers et al J. Cell Sci. 66, 383, 1984). The latter group have been able to show that this resorptive activity is not possessed by other cells of the mononuclear phagocyte series (Chambers & Horton, Calcif Tissue Int. 36, 556, 1984). More recent attempts to use other cell culture techniques to study osteoclast lineage have still had to rely on the use of cortical bone slices (Amano et al. and Kerby et al J. Bone & Min. Res. 7(3)) for which the quantitation of resorptive activity relies upon either two dimensional analysis of resorption pit areas of variable depth or stereo mapping of the resorption volume. Such techniques provide at best an accuracy of approximately 50% when assessing resorption of relatively thick substrata. In addition these analysis techniques are also very time consuming and require highly specialized equipment and training. Furthermore, the preparation and subsequent examination of bone or dentine slices is neither an easy nor practical method for the assessment of osteoclast activity.

The use of artificial calcium phosphate preparations as substrata for osteoclast cultures has also met with little success. Jones et al (Anat. Embryol 170, 247, 1984) reported that osteoclasts resorb synthetic apatites in vitro but failed to provide experimental evidence to support this observation. Shimizu et al (Bone and Mineral 6, 261, 1989) have reported that isolated osteoclasts resorb only devitalized bone surfaces and not synthetic calcium hydroxyapatite. These results would indicate that functional osteoclasts are difficult to culture in vitro.

For these reasons it appears that the currently known methods used for culturing and measuring bone cell activity cannot provide consistent or reliable reference data for meaningful and statistical analysis. Therefore these methods are not suitable for wide scale screening for the assessment of bone cell function in normal health and/or in disease. These methods are also not suitable for diagnostic testing for disease.

Culturing systems developed for general tissue culture are also not suitable for the culturing of bone cells. U.S. Pat. No. 3,726,764 describes a microbiological chamber apparatus having a sealable sidewall access port for tissue culture directly onto a base for subsequent examination and storage. U.S. Pat. No. 3,745,091 describes a biological reaction chamber apparatus having a receptacle bonded to a base by a gasket for use in tissue culture. Neither of these systems is suitable or adaptable for the successful culture and assessment of both the activities of osteoclasts and osteoblasts.

The applicant's published PCT application (WO 94/26872) described a disc coated with a calcium phosphate based thin film which could be placed into individual containment wells onto which bone cells were cultured. Although this system was successful in culturing active bone cells, the system required a great deal of handling especially with respect to the cleaning and analysis of the individual discs. There was also the problem of bone cell migration from the discs as well as some variation in the film coating present on each disc from well to well. It was apparent that this system was not suitable for a large scale screening system aimed to quantitatively assess bone cell activity and diagnose bone cell disease.

We provide in the present invention a novel and improved bone cell culture device used to assess bone cell activity. The development of this bone cell culture device overcomes the difficulties previously encountered in the culturing of functional bone cells and the reliable assessment of bone cell activity.

SUMMARY OF THE INVENTION

We have developed, in accordance with this invention, a novel multi-well bone cell culture device for use in quantitative and/or qualitative assessment of bone cell activity.

According to a first aspect of the present invention a multi well bone cell culture device is provided for use in quantitative and/or qualitative assessment of bone cell activity, said device comprising:
  a generally flat base;
  said base having a sintered thin film of calcium phosphate entities on at least one side suitable for bone cell culture;

said base having an open-ended multi chamber unit positioned on top of said film coating of said base;

means for sealing said multi chamber unit to said film coating; and said multi chamber unit sealed to said film coating forming individual containment wells.

According to a second aspect of the invention is an assay for measuring bone cell activity, said assay comprising the steps of:

providing the identified multi well bone cell culturing device of the first aspect of the invention;

inoculating at least one well of said device with a volume of bone cells;

culturing said cells in a suitable medium; and performing microscopy and/or scanning of the film component on said base to detect changes in or on the film coating between individual samples.

According to a third aspect of the invention is a drug screening assay for measuring the effects of drugs/chemicals on bone cell activity, said assay comprising the steps of:

providing the identified multi well bone cell culturing device of the first aspect of the invention;

inoculating at least two wells of said device with a volume of bone cells;

culturing said cells in a suitable medium;

addition of drug/chemical to at least one of said wells of said device; and performing microscopy and or scanning of the film component on said base to detect changes in or on the film coating between control and treated samples.

BRIEF DESCRIPTION OF THE DRAWINGS

In drawings which illustrate embodiments of the invention,

FIGS. 2A, 2B and 2C illustrates the dipping process used to coat a flat base on one surface and sintering of coated base in an oven.

FIG. 3 is a horizontal view of a base having a uniform sintered film coating on the top.

FIG. 8 is a magnified cross-section of FIG. 7 illustrating the sealant flowing onto the micro porous structure of the film coating.

FIG. 9 shows removal of a seal from the film-coated base.

DETAILED DESCRIPTION OF THE PREFERRED EMBODIMENTS

Figure 1:
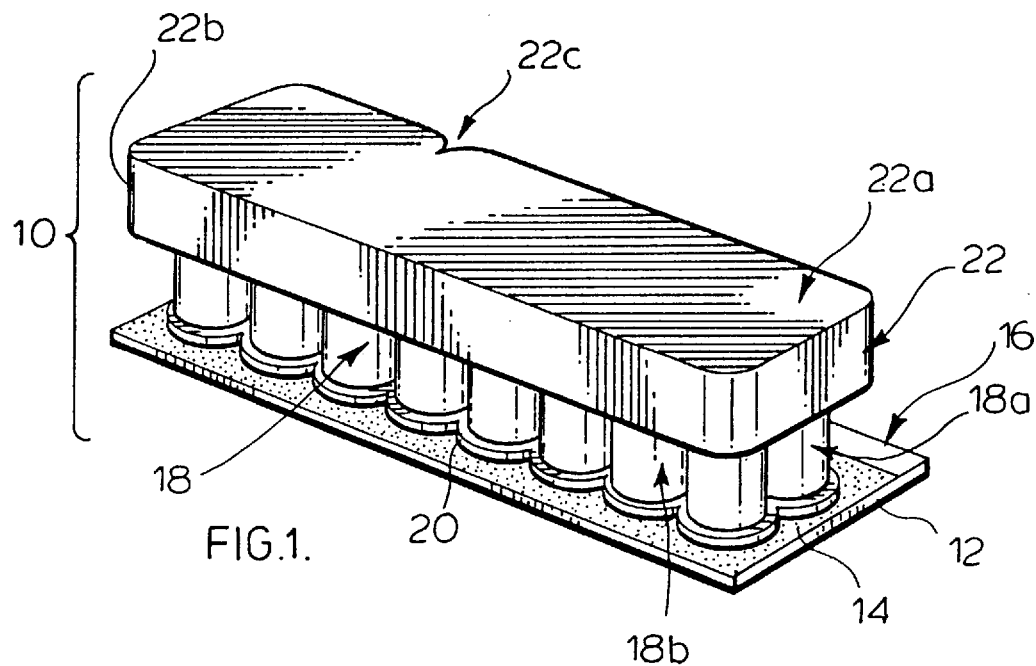
FIG. 1 is a top view of a multi-well bone cell culture device.

Referring to FIG. 1, the multi well bone cell culture device of the present invention is shown and is generally indicated by reference numeral 10. In accordance with a preferred embodiment of the present invention the multi well bone culture device 10 comprises a flat base 12 having a thin film coating 14 of calcium phosphate entities on the top of the base 12 which leaves an exposed strip on one side 16 of the base. This freely exposed surface 16 can be marked with appropriate identification markings or label affixed. Multi chamber unit 18 is placed on top of the film coating 14. The multi chamber unit 18 itself is composed of a plurality of open ended cylinders 18a. The bottom portion 18b of each cylinder 18a having an appropriate sealing device 20 described in more detail with reference to FIG. 6. The sealing device 20 seals the multi chamber unit 18 to the film coating 14. The sealing device 20 includes an appropriate sealant to effect such sealing of the multi chamber unit to the film. A lid 22 capable of covering the entire multi chamber unit is provided.

Although the preferred embodiment of this invention provides a flat base 12 of fused quartz with a distinct polish, edge bevel, flatness, and parallelism of opposing sides, it is understood by one skilled in the art that any bio compatible material which can be coated evenly with an appropriate calcium phosphate film 14, withstand both sintering and sterilization procedures such as gamma irradiation or ethylene oxide treatment, and still retain its function as a mechanical support and not be degraded or lose its structural integrity, can be used in this device. Structural integrity is considered to be a physical characteristic which is innate to the composition of the material. This would include the use of metals, polymers or ceramic materials. Glass may be used when the film material is sintered by use of a surface sintering device which heats the glass surface to a very high temperature for a brief period of time to achieve the degree of sintering necessary in providing the desired type of film 14.

The film component 14 of the device of the present invention has a granular surface, reproducible chemistry and is mechanically strong enough to withstand transport. Although the provision of pure or essentially pure calcium hydroxyapatite was understood to be the calcium phosphate entity of choice in making the film 14, we have determined that providing a mixture of calcium phosphate entities which include calcium hydroxyapatite and α-tricalcium phosphate provides the highest degree of resorption. This aspect, in combination with the other aspect of the invention in providing a thin film which permits, for example, transmittance of light, allows one to carry out diagnostic procedures to evaluate several functional properties of bone cells being cultured on the film 14 component of the device 10 in accordance with this invention.

Figure 2A:
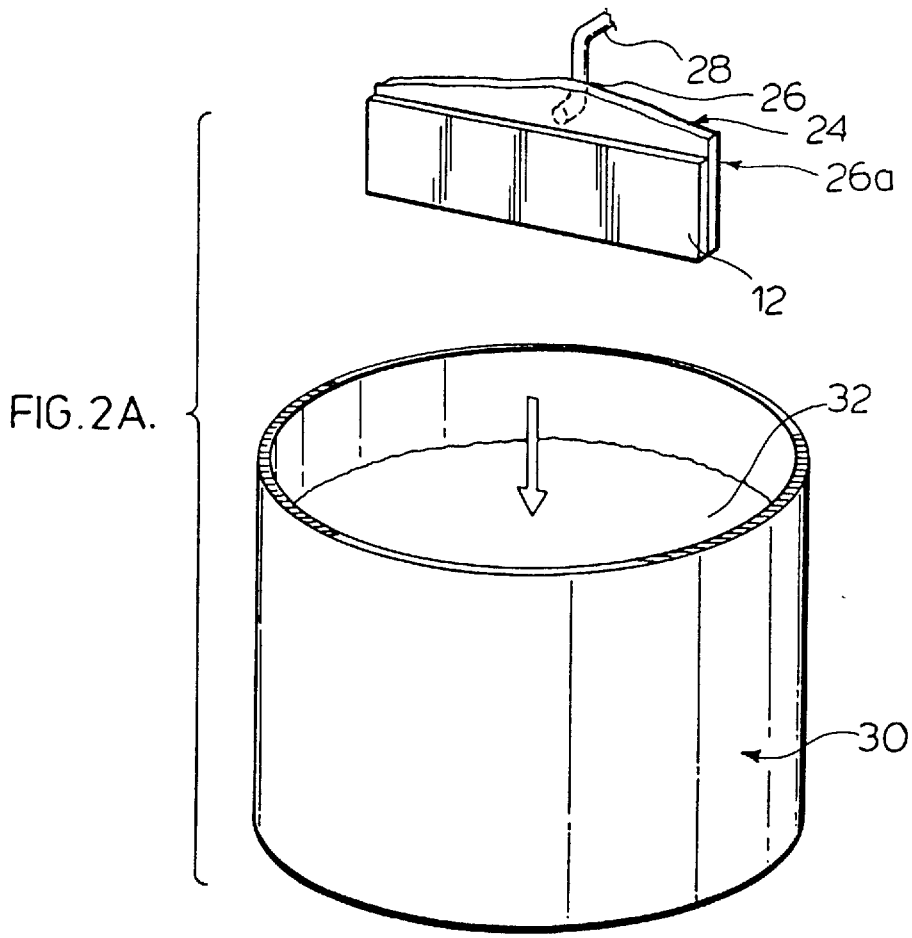

Ideally the film 14 thickness is greater than 0.1 microns because it has been found that at film 14 thicknesses less than 0.1 microns it is difficult to obtain uniform film 14 coverage, free from discrete voids. It is appreciated that thicknesses may be greater than 1 micron. The film 14 may be applied to the flat base 12 using a variety of techniques described in detail in the applicant's published PCT application (WO 94/26872). The preferred embodiment illustrated in FIG. 2A is a dipping process. In the dipping procedure the base 12 is held by a dipping device 24 having a vacuum pad 26 with planar edges 26a defining a perimeter the same size as the base 12. The pad 26 includes a centre aperture in communication with a tube 28 for applying a vacuum. The vacuum beneath the pad holds the base 12 securely onto the dipping device 24. This prevents the film 14 from coating the back of the base 12 during dipping into a vessel 30 containing the sol-gel calcium phosphate mixture 32. FIG. 2B illustrates a base 12 having an even coating of film 14 on one side. The base 12 is coated such that a thin strip of freely exposed surface 16 may be left at one side of the base 12 to allow for identification markings or to affix a label.

As depicted in FIG. 2C, sintering of the calcium phosphate film 14 on the base 12 is performed in a furnace 34 elevated to a temperature of 1000° C., or whatever other desired sintering temperature. The base 12 is sintered at that temperature for up to 1 hour after which it is allowed to cool within the furnace 34 and is finally removed. FIG. 3 illustrates that following sintering the base 12 remains flat and has retained its structural integrity. That is, the base 12 functions as a mechanical support without breaking down during the sintering process. An even thin coating of sintered film 14 remains on the base 12.

Figure 4:
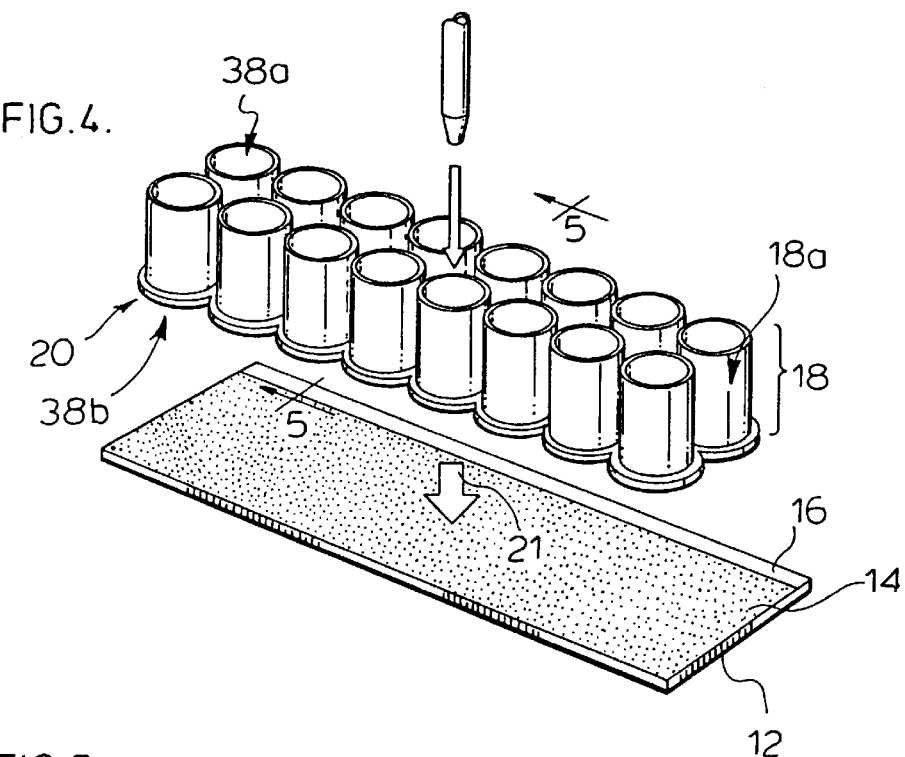
FIG. 4 illustrates positioning of an open-ended chamber unit on top of a coated base where the position of a nozzle for injection of a sealant is also shown.

The base component 12 of the present invention as depicted in FIG. 4 has the multi chamber unit 18 positioned thereon in the direction of arrow 21. The base is of a size to accommodate a multi chamber unit 18 having 16 individual cylindrical units 18a. It is however possible to fabricate a base 12 in numerous sizes and shapes onto which multi chamber units 18 may be sealed. The limiting factor is an area of base 12 onto which an even coating of calcium phosphate entities 14 can be applied.

Similarly, the multi chamber unit 18 as depicted in FIG. 4 consists of 16 individual cylindrical units 18a but this may also vary in number. The number of cylindrical units 18a sealed onto the flat base can be as few as a single chamber 18a to perhaps 96 or more depending on the size of base 12 having an even coating of film 14. In the event that a single large chamber is provided in accordance with this invention, an expanse of the film is provided to permit evaluation of long term bone cell culture and develop thereby a mass of bone cells across the entire expanse of the film. The use of a multi chamber unit 18 having specifically 16 chambers 18a is preferred because this is the number of chambers that can be fitted into standard dimensioned commercial culture plate holders. The upper limit of the number of chambers 18a which can be used per device 10 is also limited by the ability to inject a sealant 34 throughout the bottom sealing device 20 forming a leak-proof, seal. The multi-chamber unit 18 is preferably made from polystyrene, however, it is understood that any like material may be used which can be sterilized, is chemically compatible with the thin film coating 14, biocompatible, and which also can be manufactured into the unique shape containing a base sealing device 20. It is also understood that the individual chambers 18a may be of smaller or larger circumference than that depicted in the Figures. As a result, the size (volume) and/or geometry of the individually formed discrete wells 58 may also vary.

Figure 5:
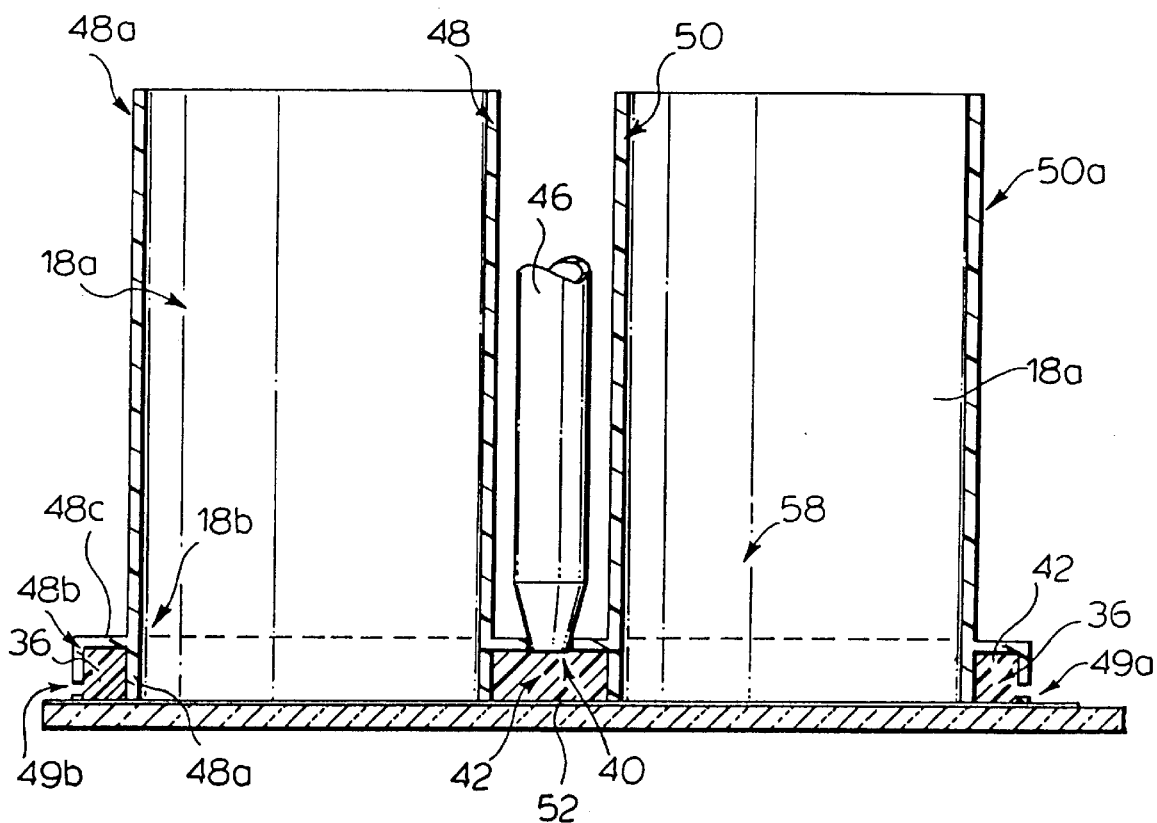
FIG. 5 is a cross-sectional view along the lines 5—5 of the multi well bone cell culture device.

As shown in FIG. 5 the multi chamber unit 18 is positioned on the base 12 and has an injection port 40 which communicates with the hollow chamber 42 in the sealing device 20. The injection port 40 accommodates a nozzle 46 which is attached to a source of sealant 36. The injection port 40 is located in between the inner walls 48 and 50 of adjacent cylindrical chambers 18a and fits into a circular opening 52 which is located in the open channel 42 of the sealing device 20. Slots 49a and 49b act as vents to allow air in the chamber 42 to escape as the sealant 36 enters. The multi chamber unit 18 is releasably clamped to the base 12 to contain the pressurized injection of sealant 36. As the sealant 36 is injected it flows throughout the channel 42 of the sealing device 20. The cross-sectional view of cylindrical unit 18a shows the channel 42 defined by two equal length opposing walls 48a and 48b and interconnecting upper wall 48c with the bottom 18b of the cylindrical unit 18a lying flat against the film 14. This forms a discrete well 58.

Figure 6:
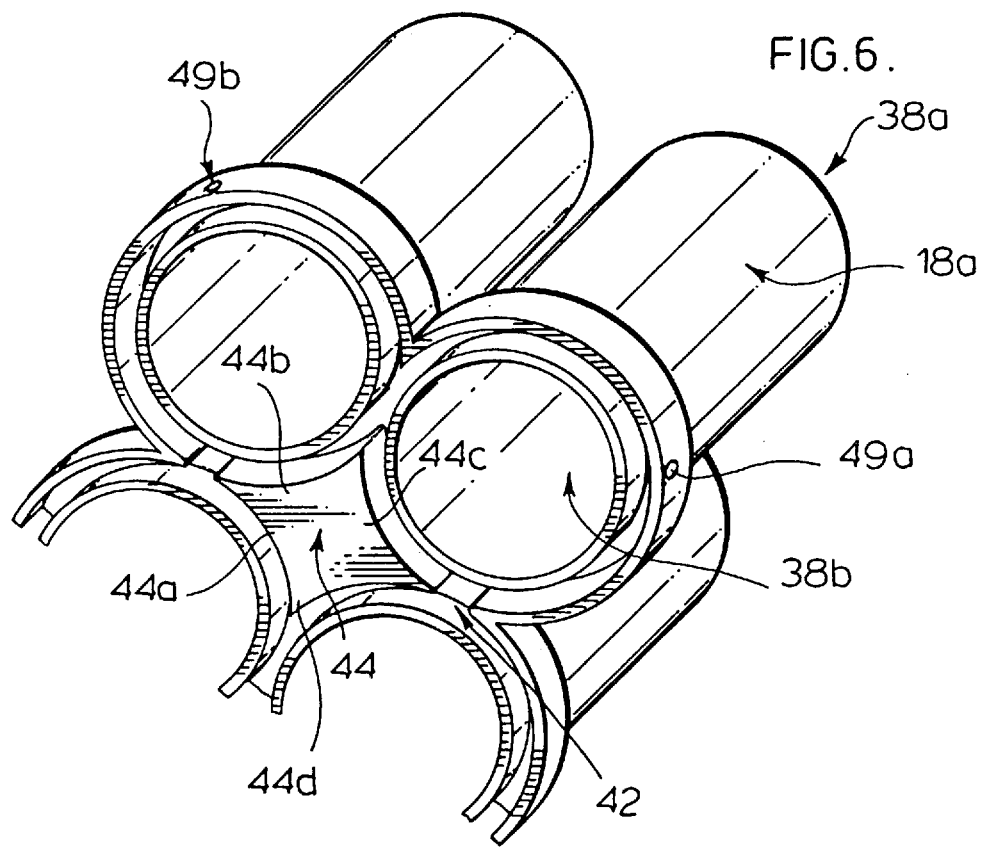
FIG. 6 is a bottom view of the hollow ended multi-chamber unit.

As shown in FIG. 6 the chambers have been illustrated as cylindrical in shape with circular openings 38a and 38b at both ends, however it is understood that the chambers 18a may be manufactured into any shape desired. The sealing device 20 located at the bottom of each cylindrical unit 18a has an open continuous channel 42 defined by walls 48a, 48b and 48c, which forms a continuous network throughout the base of each cylindrical unit 18a. Also present is an island 44 of which each of its sides 44a, 44b, 44c and 44d connects to a cylindrical unit 18a and functions to hold these together. The island 44 also helps to direct the flow of sealant 36 throughout the interconnected channels 42 of the sealing device 20.

The preferred sealant 36 for use in the device 10 of the present invention is silicone. Silicone has been accepted over many years as biocompatible for cell culture purposes. Silicone is easily injected into the channel 42 of the multi chamber unit 18 under varying pressures. As shown in FIG. 6 the silicone 36 flows throughout the channel 42 of the sealing device 20 of the cylindrical units 18a forming a continuous seal when set.

Figure 7:
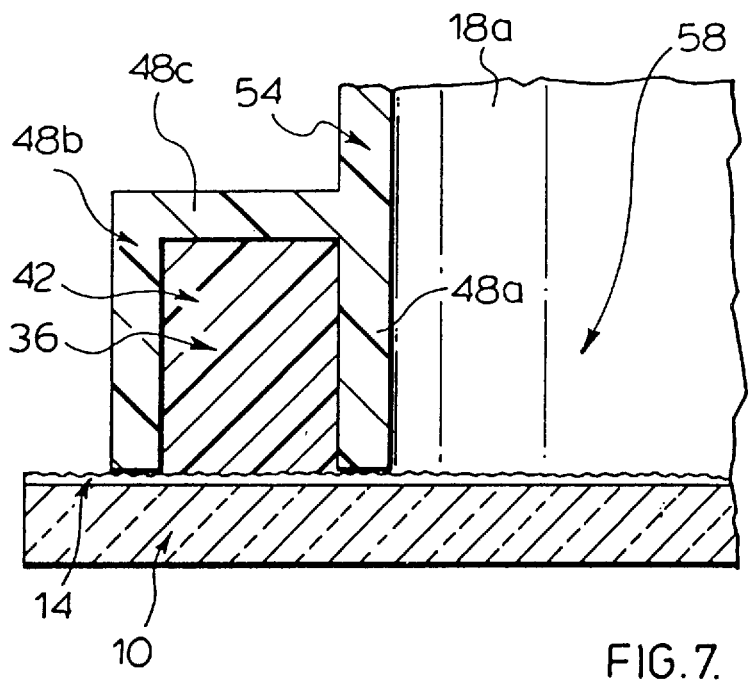
FIG. 7 is an enlarged cross-section of a chamber sealed onto a film-coated base.

FIG. 7 illustrates how the sealant 36 fills the channel 42 which is defined by the inner wall 54 which has bottom 48a of the cylindrical unit 18a and outer L-shaped wall portions 48b and 48c which sits flat on the film 14. The silicone as shown in FIG. 8 flows freely into the granular film 14 surface forming a bond between the film 14 and the inner wall 48a of the cylindrical unit 18a without affecting the film structure or composition.

Under controlled conditions, the silicone 36 is contained and does not seep into the individual containment wells 58. It forms a secure bond which also doesn't allow for migration of bone cells between wells. This is particularly advantageous over the applicant's published PCT application. The silicone 36, once set, is also sterilizabe. The sealant 36 preferentially adheres to the microporous thin film 14 coating facilitating removal of the multi well device while leaving the seal intact as desired. As shown in FIG. 9, the set silicone 36 may be removed as a single unit 60 from the surface of the film. It is understood by one skilled in the art that any material having similar characteristics to that of silicone, as defined, can also be used as a sealant 36 in this device.

A loosely fitting lid 22 to cover the wells of the device 10 is also provided in the present invention. The lid 22 is loosely fitting to provide for gaseous exchange if this is required for cell culture protocol. The lid 22 is preferably manufactured from clear polystyrene, a material which can withstand sterilization procedures. However, as one skilled in the art will appreciate any like material may also be used. The lid 22 may be manufactured in different sizes and shapes depending on the size and shape of the corresponding multi chamber unit to be covered. The preferred embodiment as depicted in FIG. 1 is a lid 22 with a flat top portion 22a which fits a multi chamber unit 18 comprising 16 individual cylindrical units 18a. The top portion 22a of the lid is flat and the sides 22b extend deep enough to cover half of the depth of the multi chamber unit 18. This is to ensure that the lid 22 is not easily knocked off. The lid 22 also has a notch 22c constructed in one longitudinal side 22b to indicate correct placement of the lid 22 onto the multi well unit 10. This ensures proper numbering of the samples.

The device of the present invention is very simple to assemble and relies on only routine laboratory equipment and techniques for use. The device is suitable for quantitative analysis of bone cell activity, and is inexpensive to fabricate but strong enough to withstand normal levels of handling. The multi-well bone cell culture device of this invention can be fabricated in a reproducible manner suitable for use as an analytical test to assay the resorptive activity of either human or animal osteoclasts or assay for the synthesis of new bone matrix by osteoblasts. The device can be used as a diagnostic test for the presence of bone cell disease. Bone cell activity can also be assessed after treatment with pharmaceutical or other bioactive agents, or mechanical, chemical or physical environmental changes. In addition, the device is economical to use in wide-scale screening and diagnosis of bone cell activity and disease as well as in clinical drug screening programs to establish compounds for treatment of bone diseases based on their effects on bone cell activity.

In each case the culture conditions may be such that osteoclasts, in either mononuclear or multi nucleate form could be expected to survive in a functional state and resorb the artificial calcium phosphate of the film. As well conditions for the successful culture by osteoblasts may also be maintained.

The device may also be used to study a process for differentiation of precursor cells, such as monocytes, into osteoclasts and monitor their resorptive activities.

The device may be used to assess the resorptive activity of osteoclasts and monitor the change in this level of resorptive activity either as a result of a disease process or the inclusion, in the culture medium, of an agent such as a drug which would influence, either directly or indirectly, osteoclastic resorptive activity. Similarly, the device may be used to assess the activity of osteoblasts in normal and in disease conditions and/or in the presence of pharmaceutical agents to influence osteoblast activity. Behaviour of bone cell activity on a modified film of this device may also be assessed. For example, organic and/or bioeffector molecules may be incorporated in or provided on the film to determine the effect such molecules have on cultured bone cells such as osteoclasts and osteoblasts.

The device may be used as a means of quantifying the resorptive activity of osteoclasts or the synthesizing activity of osteoblasts. Such activity analysis may occur under continuous real-time monitoring, time-lapse intervals or end-point determination. The steps in establishing osteoclast/osteoblast activity are common to each of the above monitoring schedules in that bone cells (either animal or human) are cultured, in specific conditions, into wells of the devices. The culture period is from several hours to many days (the optimum time is cell species and protocol dependent), during which time the extent of osteoclast/osteoblast activity may be continuously monitored, periodically monitored, or simply not monitored on an on-going basis in favour of final-end-point determination.

Several different osteoclast activity analysis techniques may be employed independently or in combination. The premise of each technique is the quantification of the degree of resorption of the calcium phosphate thin film surface by the osteoclast cells in culture. In detecting the resorption occurrence and in view of the variety of techniques for doing so, it is understood that, by virtue of the thin film component of this invention, a detection can now be made of the physical disappearance of the calcium phosphate entities. The physical disappearance can now be detected either directly or indirectly. Osteoblast activity may be analysed by fluorescence using tetracycline as a label, by simple densitometry, or by radioactive labelling.

An example of an end-point optical assessment of the resulting surface involves performing microscopy and/or scanning of the film defined by each chamber. Such microscopy and/or scanning may include the removal of the medium from each culture well as well as the removal of all cells from the surface of the film. The multi chamber unit is removed followed by the stripping off of the solidified sealant from the film. This leaves only the film coated base in which resorption of calcium phosphate entities or secretion of organic bone matrix has occurred in the discrete well areas. The simple dismantling of the multi well bone cell culture device leaving a single base with multiple sample areas is extremely advantageous over any other known bone cell culture method because it makes the analysis and handling of numerous samples much easier and more suited for large scale sample analysis. The film coated base before or after the detailed treatment to remove the chambers is analysed using light microscopy, transmission electron microscopy, scanned by automated image analysis, or subjected to densitometric reading to quantitatively and/or qualitatively characterize film structure and/or composition. Details and descriptions of specific analysis techniques as well as modes of quantification of resorbed calcium phosphate entities are provided in the applicant's published PCT application (WO 94/26872).

It is recognized that the above techniques may be automated to increase the efficiency of the analysis procedure. The extent of automation may extend from the culture techniques to the analysis of osteoclast and/or osteoblast activity. In addition, such automation may be configured to link with a computerized database for statistical analysis of resulting data.

Furthermore, it is recognized that several film coated bases may be evaluated in unison such that numerous samples may be assessed at any given time.

A comprehensive evaluation of osteoclasts requires a standardized cell culture exposure protocol. This final analysis requires the removal of all cellular material so that the surface can be freely assessed. Since the exposure time is then fixed in a given comparative study, the degree of resorption occurring on the device of this invention can be expressed as the percentage of the film removed by the osteoclasts versus the total film exposed to the media. As the film is thin, the amount of material removed can be related to the plan area of the created voids. This accurate two-dimensional assessment of a three-dimensional resorption event greatly simplifies the techniques required to assess the degree of resorption, versus that necessary to evaluate conventional bone slices that exhibit complex irregular three-dimensional resorption pits of no fixed depth. In the use of the device of this invention, a high degree of resorption is expressed as large often interconnected voids in the film with characteristic organic perimeter outlines (of a scalloped nature). In contrast, a low degree of resorption is expressed as infrequent pinholes in the film creating a punctate topography. Build-up of bone-like material on the film by osteoblasts may be expressed elevations on the surface of the film The multi-well bone cell culture device, in accordance with this invention, significantly advances the study and understanding of bone cell functional properties. The device, as provided in accordance with this invention, permits the culture of bone cells thereon where the film composition is uniform between different wells contained within the same device as well as between separate devices. This allows for uniform and consistent assays to be performed which produces superior and statistically significant data. The film allows for resorption of the calcium phosphate entities as well as for the production of new bone matrix to be detected on the film.

A significant benefit of the invention is providing a thin film of calcium phosphate entities on a single supporting substrate which can hold several samples at a time including the co-culturing of osteoblasts and osteoclasts using the same film surface. For example, in three adjacent wells, there may be respectively a culture of osteoclasts, osteoblasts and a suitable control cell culture. In this manner physiologically significant comparisons of osteoblast and osteoclast function under similar conditions can be performed.

The device as described herein prevents the migration of bone cells from the surface of the film. Overall, the multi well bone cell culture device is easy to handle and use and is economical for large-scale screening and diagnosis of abnormal bone cell activity which is critical for the identification of and effects of drugs important to regulate bone cell activity and treat bone cell diseases.

Although preferred embodiments of the invention are described herein in detail, it will be understood by those skilled in the art that variations may be made thereto without departing from the spirit of the invention.

We claim:

1. A multi well bone cell culture device for use in quantitative and/or qualitative assessment of bone cell activity, said device comprising:
   a flat base of quartz material having a sintered thin film of uniform thickness with a granular surface and reproducible chemistry of calcium phosphate entities on one side for culturing bone cells;
   said base having an open ended multi-chamber unit comprising individual adjacent cylindrical chambers interconnected at their common sidewall, the bottom of said chambers lying flat against said film and having a hollow continuous chamber containing a sealant to bond to the surface of the film to form a leak proof seal and to prevent the migration of cultured bone cells between chambers;
   the multi chamber unit forming discrete wells on the film coated base occupying specific areas on said film wherein said film composition is uniform between different wells facilitating easy and accurate comparison of bone cell activity from well to well; and
   a transparent lid for covering said device.

2. A multi well bone cell culture device of claim 1, wherein said sintered film-coated base withstands sterilization methods selected from gamma radiation or ethylene oxide treatment and retains its structural integrity.

3. A multi well bone cell culture device of claim 1, wherein said multi-chamber unit component is made from a biocompatible, film-compatible and sterilizable plastic such as polystyrene.

4. An assay for measuring bone cell activity, said assay comprising the steps of:
   providing the culturing device of claim 1;
   inoculating at least one well of said device with a volume of bone cells;
   culturing said cells in a suitable medium; and
   performing microscopy and/or scanning of the film component on said base to detect changes in or on the film coating between individual samples.

5. An assay of claim 4, wherein said step of performing microscopy and/or scanning includes the additional steps of:
   removing the multi-chamber unit;
   removing the seal; and/or
   removing remaining cells.

6. An assay of claim 4, wherein said assay is diagnostic to determine quantitative aspects of measuring bone cell activity.

7. An drug screening assay for measuring the effects of drugs/chemicals on bone cell activity, said assay comprising the steps of:
   providing the culturing device of claim 1;
   inoculating at least two wells of said device with a volume of bone cells;
   culturing said cells in a suitable medium;
   addition of drug/chemical to at least one of said wells of said device;
   performing microscopy and/or scanning of the film component on said base to detect changes in or on the film coating between control and treated samples.

8. A drug screening assay of claim 7, wherein said step of performing microscopy and/or scanning includes the additional steps of:
   removing the multi-chamber unit;
   removing the seal; and
   removing remaining cells.

* * * * *